United States Patent [19]

Talapin et al.

[11] Patent Number: 4,971,079

[45] Date of Patent: Nov. 20, 1990

[54] PHARMACEUTICAL PREPARATION POSSESSING ANTINICOTINE EFFECT AND METHOD OF PRODUCING SAME IN A GUM CARRIER

[76] Inventors: Vitaly I. Talapin, ulitsa Tikotskogo, 42, kv. 12; Elena A. Rimzha, prospekt Pushkina, 33, kv. 52; Fedor N. Kaputsky, ulitsa Kuznechnaya, 3, kv. 83; Viktor A. Stelmakh, ulitsa Yanki Kupaly 11, kv. 74; Galina V. Ustichenko, ulitsa Odoevskogo 36, kv. 141; Tatyana L. Yurkshtovich, prospekt Lenina, 12, kv. 17, all of Minsk, U.S.S.R.

[21] Appl. No.: 23,914

[22] Filed: Mar. 5, 1987

Related U.S. Application Data

[63] Continuation of Ser. No. 552,121, filed as PCT SU83/00004 on Feb. 22, 1983, published as WO83/02892 on Sep. 1, 1983, abandoned.

[30] Foreign Application Priority Data

Feb. 22, 1982 [SU] U.S.S.R. ................................ 3425002
Mar. 16, 1982 [SU] U.S.S.R. ................................ 3425001
Jun. 7, 1982 [SU] U.S.S.R. ................................ 3470509
Feb. 22, 1983 [WO] PCT Int'l Appl. ... PCT/SU83/00004

[51] Int. Cl.$^5$ .......................... A24B 47/00; B32B 3/14
[52] U.S. Cl. .................................. 131/359; 131/270; 426/3; 428/48; 428/197
[58] Field of Search ............... 131/359, 276, 271, 270, 131/273; 428/48, 197; 426/3

[56] References Cited

U.S. PATENT DOCUMENTS 3,063,905 11/1962 Novak ..................................... 424/19
3,818,107 6/1974 Yolles ..................................... 426/3
3,877,468 4/1975 Lichtneckert et al. ............... 131/270
3,901,248 8/1975 Lichtneckert et al. ............... 131/359
4,195,645 4/1980 Bradley ................................ 131/337

FOREIGN PATENT DOCUMENTS 4627M 1/1967 France .

OTHER PUBLICATIONS

Chem. and Pharm. J.; "Anabosine . . . "; vol. XII, No. 2; pp. 149-152; Nasirou et al.; 1978.
"Medical Preparations"; pp. 206-207; Urvantsev; Nauka; Tekhnika Pub.; Minsk; 1973.
Chem. Abst., vol. 79; 83451c; "Sub. for Tob. Smoking"; 1973; Ferno et al.
"Org. Chem."; Feiser and Feiser; pp. 826-827; 1956; Reinhold Pub. Co.; NY.

*Primary Examiner*—V. Millin
*Attorney, Agent, or Firm*—Emmanuel J. Lobato; Robert E. Burns

[57] ABSTRACT

A pharmaceutical preparation, in a chewing gum carrier, possessing an antinitocine effect which comprises a biologically resorbable polymeric vehicle containing a cation-exchange group and modified thereat by an antinicotine-action action alkaloid in the following proportions thereof, percent by mass: antinitocine-action alkaloid 2.5-40.0 polymeric vehicle the balance. The method of producing the preparation comprises reacting a biologically resorbable polymeric vehicle containing a cation-exchange group with an antinicotine-action alkaloid in an aqueo-organic medium at a volume ratio of the aqueous and organic phases of 1-15:1-24 respectively and at a temperature within the range of from 8° to 22° C.

12 Claims, No Drawings

PHARMACEUTICAL PREPARATION POSSESSING ANTINICOTINE EFFECT AND METHOD OF PRODUCING SAME IN A GUM CARRIER

Ser. No. 06/552,121 filed as PCT SU83/00004 on Feb. 22, 1983, published as WO83/02892 on Sep. 1, 1983, now abandoned.

FIELD OF THE INVENTION

The present invention relates to the art of medicine and, more particularly, it relates to a pharmaceutical preparation possessing an antinicotine effect and to a method of producing same.

BACKGROUND OF THE INVENTION

Combatting tobacco smoking is nowadays an urgent social problem. The World Health Organization, while stressing the major role of smoking in origination and development of cardio-vascular and oncological diseases, emphasizes an insistent need in decisive measures to be elaborated against smoking.

Modern medical practice, in addition to preventive measures, is in possession of certain methodical approaches and methods of combating the tobacco smoking. These cover substitution of nicotine-containing cigarettes with various confectionery products—candies, pills, as well as chewing forms—pastilles and chewing gum.

In combating tobacco smoking various distracting means are widely employed such as beads, cinema, reading, sports and the like (F. J. Chicou, 1975; R. Flurin et al. 1976; WHO Techn. Rep. Ser. 1975).

In a number of countries such as United States, Great Britain, France, Canada, Sweden and others a whole number of programs are under way to slow-down the consumption of tobacco goods. These comprise limitation of growth rates of domestic tobacco sales at the account of promoting their export, restriction of advertizing, reduction of the content of resinous substances and nicotine in sigarettes, marking thereof with indication of the content of these substances and the like (J. Joannou "Peut-on conjuree le peril tabagique", Vie med., 1979, 60, No. 9, 697–698).

As tobacco substitute in the USA, leaves of other night-shade plants are used in addition to tobacco such as potato, tomato, eggplant, digitalis and other plants (cf. Labadie L.C. Peut-on supprimer les facteurs de risque en bronchopatie chronique et en particulier le tabac", Mediater, med., 1976, 4, No. 112, 97, 99).

The tobacco goods proper are being modified in structure, e.g. by creation of filters, special paper treatment and the like (cf. U.S. Pat. No. 4,011,141; Beil M. "Zutverschmutzung durch", Prax. Pheumol.,-1975, 29, Nr. 7, 403–412).

All these measures are but palliatives which do not fully solve the problem of a complete refusal from smoking.

For the treatment of persons with a long-time and strong nicotine dependable of the organism and if the person himself is incapable of giving it up, medicamental methods have been developed. All the pharmaceutical compositions employed for the treatment of chronic nicotinism can be divided into two groups. The first covers salts of silver, iron and copper. These substances are employed to develop a negative reflex to smoking, usually in the form of a solution, or in some countries (Sweden, Denmark, Austria) they are incorporated in chewing gum compositions. The resultant reflex is based on the appearance of a strong unpleasant taste in the mouth during smoking after a preliminary rinsing of the mouth cavity with solutions of salts, or after the use of a chewing gum containing such salts (Ser. No. Nasirov et al. "Anabasine Hydrochloride—New Antismoking Agent", Chemico-Pharmaceutical Journal, vol. XII, 1978, No. 2, 149–152/ in Russian/).

The second group of smoking-combating agents comprises substances of an alkaloidal nature possessing an effect on H-cholinoreactive systems of the organism similar to that of nicotine. The mechanism of their effect is caused by their structural similarity with nicotine and possibility of the emergence of a "competitive" antagonism between these alkaloids (F.R. Khalikova, S. H. Nasirov "On pharmacology of the Alkaloid Anabasine and some Polymeric and Copolymeric Derivatives Thereof", in Coll. "Pharmacology of Vegetable Compounds", Proceedings of Tashkent University, issue 457, 1973, p. 5–16).

Such substances are cytisine, lobeline and a novel domestically developed preparation - anabasine hydrochloride. Cytisine, for example, is incorporated into the composition of a known preparation "Tabex" (Bulgaria); it is also the basis of so-called "Kuz'-manovich tablets" (Yugoslavia) and of a domestic preparation "Lobesil" containing alkaloid lobeline (cf. Yu.D. Goldovt et al. "Pharmaceutical Preparations" Minsk, 1973, p.206-207; Orlovsky L.V. "Latent danger—on the detrimental effects of smoking", Moscow, "Znanije" (Knowledge) Publishers, 1977, p.64).

However, the efficiency of enteral administration of tabletted pharmaceutical preparations is insufficient.

The short-time effect of tabletted pharmaceutical preparations caused by decomposition thereof upon passing through the gastro-enteral and hepatic barriers creates practical inconveniences associated with the necessity of multiple administration of tablets (5–8 times a day) which, in turn, results in increased daily and course doses of the preparations.

The enteral administration of alkaloid medicated compounds can cause an undesirable effect on the mucous membrane of the stomach, thus resulting in painful symptoms in patients suffering from peptic ulcer (cf. S.H. Nasirov et al. "Chemico-Pharmaceutical Journal" vol. XII, 1978, No. 2, p. 149-152).

DISCLOSURE OF THE INVENTION

The present invention is directed to the provision of a pharmaceutical preparation possessing an antinicotine effect by way of modification of a polymeric vehicle with an antinicotine-action alkaloid which would ensure a higher efficiency of treatment therewith simultaneously with reduction of its single, daily, and course doses. The term "antinicotine" as used herein, refers to the capability of suppressing the desire for nicotine.

This object is accomplished by that the pharmaceutical composition possessing the antinicotine effect according to the present invention contains a biologically absorbable polymeric vehicle with a cation-exchange group at which it is modified by an antinicotine-action alkaloid, the components being present in the following proportions, percent by mass: antinicotine-action alkaloid 2.5–40.0 polymeric vehicle the balance.

The use of the pharmaceutical preparation according to the present invention ensures a protected local effect on the same receptor zones of the mucous membrane of the mouth cavity as nicotine upon smoking, it provides conditions for the alternative displacement of smoking, as well as for absorption of the antinicotine-action alkaloid from the mucous membrane of the mouth thus excluding the decomposing effect of gastro-enteral enzymes, as well as avoiding the barrier function of liver.

Such properties of the pharmaceutical composition according to the present invention make it possible to substantially (by 4–12 times) lower the total (course) dose of the antinicotine alkaloid simultaneously with improving the treatment efficiency.

To control and adjust the rate of absorption of the pharmaceutical composition in the mouth cavity and ensure the required duration of its oral action, according to the present invention, it is advisable that as the polymeric vehicle contain monocarboxycellulose, carboxymethylcellulose, phosphatecellulose, hydroxystarch, dicarboxydextran, polyvinylsulphate, polymethacrylic acid which are modified by cytisine, anabasine hydrochloride or lobeline hydrochloride.

The present invention also relates to a method for producing the pharmaceutical composition possessing an antinicotine effect, wherein according to the present invention a biologically absorbable polymeric vehicle containing a cation-exchange group is reacted with an antinicotine-action alkaloid in an aqueoorganic medium at a volume ratio between the aqueous and organic phases of 1–15:1–25 respectively and at a temperature of from 8° to 22° C., at a pH of the medium preferably within the range of from 6.5 to 8.5.

The method according to the present invention makes it possible to provide a preparation with a high concentration of the active principle therein (up to 40% by mass), to substantially extend the duration of its oral effect.

It is advisable that the aqueo-ethanolic or aqueo-propanolic medium be used to provide favourable conditions for the manufacture of antinicotine-effect pharmaceutical preparations.

To administer the pharmaceutical preparation according to the present invention in the form of a chewing gum, it is advisable that it additionally contain a base, a plasticizer, an aromatizing agent, syrup and sugar powder at the following proportions of the components, percent by mass:

| polymeric vehicle modified by antinicotine-effect alkaloid | 0.05–4 |
| --- | --- |
| base | 20–31 |
| plasticizer | 1–1.5 |
| syrup | 12–19 |
| aromatizing agent | 0.4–0.6 |
| sugar powder | the balance |

The use of such pharmaceutical chewing gums makes more convenient the medical administration of the preparation and improves conditions for the alternative displacement of smoking simultaneously with lowering fatiguability upon both physical and mental work.

To enhance the antiabstinent effect, i.e. alleviation of the abstinence syndrome, of the pharmaceutical antinicotine preparation according to the present invention, it is also desirable that it contain phosphatecellulose modified by pyrroxane and taken in an amount of from 5 to 10% of its total mass. To improve the taste characteristics of the pharmaceutical preparation according to the present invention and prevent the hypovitaminous state in a smoker, it is advisable that it contain aminocarboxycellulose modified with ascorbic acid and taken in an amount of from 5 to 15% of its total mass.

BEST MODE FOR CARRYING OUT THE INVENTION

As has been mentioned hereinbefore, the pharmaceutical antinicotine preparation according to the present invention contains a biologically absorbable polymeric vehicle containing a cation-exchange group and modified at this group by an antinicotine-action alkaloid at the following proportions of the components, percent by mass:

| antinicotine-action alkaloid | 2.5–40 |
| --- | --- |
| polymeric vehicle | the balance |

Properties of the pharmaceutical preparation, in particular duration of its oral effect, depend on the mode of its production, a final pharmaceutical form and on the properties of the employed polymeric carrier. As the polymeric vehicle use can be made of any pharmaceutically acceptable vehicle of the type of modified natural or synthetic high-molecular compounds capable of reacting with antinicotine-action alkaloids according to the cation-exchange reaction.

To obtain high-efficiency preparations, it is advisable to make use of, as the polymeric vehicle, monocarboxycellulose, carboxymethylcellulose, phosphatecellulose, polyvinylsulphate, polymethacrylic acid, dicarboxydextrane, hydroxystarch. As the active principle the pharmaceutical composition according to the present invention can incorporate any pharmaceutically acceptable antinicotine-action alkaloid such as cytisine, anabasine, lobeline and salts thereof. The content of the antinicotine-action alkaloid in the preparation is 2.5 to 40% by mass. The upper limit is determined by the limit of saturation of the polymeric carrier with the alkaloid, while the lower limit is characterized by the possibility of using the preparation in different pharmaceutical forms, in particular in the form of pharmaceutical films, tablets for retrobuccal administration, chewing tablets. In the form of various tablets it is possible to lower the concentration of the antinicotine-action alkaloid in the pharmaceutical preparation to the level ensuring its single therapeutic dose in a formed piece.

We have studied IR-spectra of the pharmaceutical composition according to the present invention in order to determine the ion-exchange character of interaction of the antinicotine-action alkaloid with the polymeric vehicle. It has been found that the intensity of the absorption band at 1730 cm$^{-1}$ of the stretching vibration of the carboxy group is lowered. At the same time, there appear absorption bands of 1430–1610 cm$^{-1}$ of symmetric and asymmetric stretching vibrations of the carboxylase ion which clearly points to the ion-exchange character of interaction between the above-mentioned components.

To obtain an anti-nicotine effect preparation according to the present invention, a method is provided which resides in that a biologically asborbable polymeric vehicle containing a cation-exchange group is reacted with an antinicotine-action alkaloid in an aqueo-organic medium at a ratio between the organic and aqueous phases of 1–25:1–15 respectively, at a temperature of from 8° to 22° C.; it is preferable to use an aqueo-ethanolic or aqueo-isopropanolic medium at a pH of the medium of from 6.5 to 8.5.

These process parameters make it possible to produce a pharmaceutical preparation with predetermined physico-chemical properties, with a high degree of saturation of the polymeric vehicle with the antinicotine-action alkaloid and possessing an extended time of its absorption within the mouth cavity.

The present invention also relates to a pharmaceutical preparation possessing an antinicotine effect which can be used as a chewing gum. It also contains a chewing mass comprising a base, a plasticizer, syrup, aromatizing agent, sugar powder at the following proportions of the components, percent by mass:

| | |
|---|---|
| polymeric vehicle modified by an antinicotine-action alkaloid | 0.0005–4 |
| base | 20–31 |
| plasticizer | 1–1.5 |
| syrup | 12–19 |
| aromatizing agent | 0.4–0.6 |
| sugar powder | the balance |

We have found that the polymeric vehicle modified by an antinicotine-action alkaloid when introduced into the chewing mass does not chemically react with its ingredients or become inactivated thereby. Use may be made of both natural, synthetic bases or mixtures thereof.

The pharmaceutical preparation of the above composition is produced by way of physico-mechanical intermixing of the components. Additional high-molecular compounds modified by pyrrozane and ascorbic acid can be introduced into the preparations in the form of a chewing gum to impart thereto a higher abstinent effect and ability of preventing Chypovitaminosis developing in smokers.

Toxicity of antinicotine alkaloids is not changed upon their chemical interaction with the polymeric vehicles according to the present invention.

The antinicotine-effect pharmaceutical preparation does not have a local irritating action and allergenic activity. To facilitate giving-up smoking and favour the treatment of chronic nicotinism, the preparation in the form of pharmaceutical films or oraleffect tablets is kept in the mouth cavity till a complete absorption, during which an antinicotine alkaloid is liberated into the mouth cavity for a long time (up to 12 hours). This ensures a long-time blocking of receptors of the mouth cavity reacting with nicotine and absorption of the alkaloid avoiding the gastroenteral barriers and makes it possible to improve efficiency of the treatment simultaneously with lowering single, daily and course doses of the antinicotine alkaloids.

The incorporation of the pharmaceutical preparation according to the present invention into a chewing gum composition enhances conveniency of its medical application and in some cases improves the treatment efficiency due to a more pronounced alternative displacement of smoking.

Chemical studies of the pharmaceutical preparation possessing antinicotine effect according to the present invention with the oral mode of administration thereof demonstrate a higher efficiency thereof in comparison with other known preparations at a simultaneous considerable lowering of the amount of the antinicotine alkaloid introduced into the organism. This also enables a substantially full elimination of the damaging effect of the alkaloid on the mucous membrane of the stomach and intestine and considerably lowered unfavourable effect thereof on the liver tissue.

The antinicotine-effect preparation according to the present invention weakens inclination towards smoking and diminishes vegetative and other disturbances usually accompanying the period of giving-up smoking.

The treatment efficiency is usually about 90–96%, the therapeutic effect of the preparation being enhanced at a resolute decision of a smoker to give up smoking.

EXAMPLE 1

2.5 g of cellulose are oxidized with a 11% solution of $N_2O_4$ in carbon tetrachloride (bath modulus is 1:50) for 24 hours at room temperature. The obtained sample is kept in the air for 30 minutes, washed with distilled water till disappearance of the qualitative reaction on $NO_2^-$ and $NO_3^-$ ions, dried at room temperature to the air-humid state. The content of carboxy groups in the resulting monocarboxycellulose is 8.4% by mass.

Monocarboxycellulose taken in the amount of 2 g is placed into 100 ml of a 1% aqueo-ethanolic solution (1:8 by volume) of cytisine, added with 2 ml of a 1N solution of hydrochloric acid to the pH of 6.5 and the mixture is kept for 2 hours at the temperature of 15° C. The thus-obtained sample is dried at room temperature till the air-humid state. The content of combined cytisine determined by the Kjeldahl method is 10% by mass. The time of absorption of the pharmaceutical preparation in the mouth cavity is 12 hours.

EXAMPLE 2

Monocarboxycellulose prepared as described in the foregoing Example 1 and taken in the amount of 2 g is placed into a reaction vessel with 100 ml of a 1% aqueo-ethanolic (1:2 by volume) solution of cytisine and kept for 3 hours at the temperature of 12° C. and pH=8.5. The resulting sample is dried at room temperature till the air-humid state. The content of combined cytisine determined by the Kjeldahl method is 25.9% by mass. The time of absorption of the pharmaceutical preparation in the mouth cavity is 10 hours.

EXAMPLE 3

Monocarboxycellulose prepared as in Example 1 and taken in the amount of 2 g is placed into 100 ml of a 1% aqueo-ethanolic solution (1:3.5 by volume) of cytisine, added with 1 ml of a 1N solution of HCl to the pH=7.1, kept for 4 hours at the temperature of 8° C. The resulting sample is dried at room temperature to the air-humid state. The content of combined cytisine determined by the Kjeldahl method is 40% by mass. The time of absorption of the pharmaceutical composition in the mouth cavity is 8 hours.

EXAMPLE 4

Carboxymethylcellulose taken in the amount of 2 g is placed into 100 ml of a 1% aqueo-isopropyl (1:2 by volume) solution of anabasine hydrochloride, added with 4.8 ml of 0.1N solution of NaOH to the pH=6.5, kept for 3 hours at the temperature of 8° C. The resulting sample is dried at room temperature to the air-humid state. The content of combined anabasine determined by the Kjeldahl method is 10% by mass. The time of absorption of the pharmaceutical composition in the mouth cavity is 4 hours.

EXAMPLE 5

Monocarboxycellulose prepared as in Example 1 hereinbefore and taken in the amount of 2 g is placed into 100 ml of a 1% aqueo-isopropyl (1:3 by volume) solution of cytisine at the pH=8.5 and at the temperature of 15° C.; the time of residence is 4 hours. The resulting sample is dried at room temperature to the air-humid state. The content of combined cytisine determined by the Kjeldahl method is equal to 33.8% by mass. The time of absorption of this preparation according to the present invention in the mouth cavity is equal to 9 hours.

EXAMPLE 6

Cellulose taken in the amount of 2.5 g in the form of cotton coarse calico is oxidized with a 14% solution of $N_2O_4$ in $CCl_4$ (bath modulus is 1:50) for 24 hours at room temperature. The resulting sample is vented in the air for 30 minutes, rinsed with distilled water till the disappearance of the qualitative reaction for $NO_2^-$, $NO_3^-$ ions, dried at room temperature to the air-humid state. The content of carboxy groups in the resulting monocarboxylcellulose is 8.4% by mass.

Monocarboxycellulose taken in the amount of 2 g is placed in 55 ml of an aqueo-ethanolic (10:1 by volume) solution containing 0.5 g of anabasine hydrochloride, kept in this solution for 5 hours under continuous stirring at room temperature. The resulting sample is dried at room temperature to the air-humid state. The content of combined anabasine determined by the Kjeldahl method is 2.5% by mass. The time of absorption of the preparation in the mouth cavity is 1.7 hours.

EXAMPLE 7

Monocarboxycellulose prepared in a manner similar to that described in Example 1 hereinbefore and taken in the amount of 2 g is placed into 100 ml of an aqueo-ethanolic (1:2 by volume) solution of anabasine hydrochloride, kept in this solution for 5 hours under continuous stirring at room temperature The resulting sample is dried at room temperature to the air-humid state. The content of combined anabasine determined by the Kjeldahl method is 7.3% by mass. The time of absorption of the preparation in the mouth cavity is 5 hours.

EXAMPLE 8

Cellulose taken in the amount of 2.5 g in the form of cotton coarse calico is oxidized with a 35% solution of $N_2O_4$ in $CCl_4$ (bath modulus is 1:50) for 24 hours at room temperature. The resulting sample is vented for 30 minutes, rinsed with distilled water till the disappearance of the qualitative reaction for $NO_2^-$ and $NO_3^-$ ions, dried at room temperature to the air-humid state. The content of carboxy groups in the thus-prepared monocarboxycellulose is 14.5% by mass.

The resulting monocarboxycellulose taken in the amount of 2 g is placed into 100 ml of an aqueous ethanolic (1:4 by volume) solution of anabasine hydrochloride containing 1.8 g of this alkaloid, kept in this solution for 5 hours under continuous stirring at room temperature. The thus-obtained sample is dried at room temperature to the air-humid condition. The content of combined anabasine determined by the Kjeldahl method is 14.8% by mass. The time of resorption of the preparation in the mouth cavity is 2.5 hours.

EXAMPLE 9

Monocarboxycellulose taken in the amount of 2 g and prepared in a manner similar to that described in the foregoing Example 8 is placed into 100 ml of an aqueo-ethanolic (10:1 by volume) solution containing 0.2 g of cytisine, kept in this solution for 5 hours at room temperature under continuous stirring. The resulting sample is dried at room temperature to the air-humid state. The content of combined cytisine is 3.0% by mass. The time of absorption of the preparation in the mouth cavity is 3.2 hours.

EXAMPLE 10

Monocarboxycellulose taken in the amount of 2 g and prepared as in Example 8 hereinbefore, is placed into 55 ml of an aqueo-ethanolic (15:1 by volume) solution containing 0.4 g of cytisine, maintained in this solution for 5 hours at room temperature under continuous stirring. The thus-produced sample is dried at room temperature to the air-humid state. The content of combined cytisine is equal to 8.2% by mass. The time of absorption of the preparation in the mouth cavity is 2 hours.

EXAMPLE 11

Monocarboxycellulose taken in the amount of 2 g and prepared as in Example 6 is placed into 55 ml of an aqueo-ethanolic (10:1 by volume) solution containing 0.5 g of cytisine, kept in this solution for 5 hours at room temperature and under continuous stirring. The resulting sample is dried at room temperature to the air-humid state. The content of combined cytisine is 15.1% by mass. The time of absorption of the pharmaceutical preparation in the mouth cavity is 3 hours.

EXAMPLE 12

Monocarboxycellulose taken in the amount of 2 g and prepared in a manner similar to that described in Example 8 hereinbefore is placed into 100 ml of an aqueo-ethanolic (1:10 by volume) solution containing 0.9 g of lobeline hydrochloride, kept in this solution for 5 hours at room temperature under continuous stirring. The thus-obtained sample is dried at room temperature to the air-humid state. The content of combined lobeline hydrochloride is 2.9% by mass. The time of absorption of the pharmaceutical preparation in the mouth cavity is 1.8 hours.

EXAMPLE 13

Monocarboxycellulose taken in the amount of 2 g and prepared in a manner similar to that described in Example 8 hereinbefore is placed into 100 ml of an aqueo-ethanolic (1:20 by volume) solution containing 1.4 g of lobeline hydrochloride; kept in this solution for 5 hours at room temperature under continuous stirring. The resulting sample is dried at room temperature to the air-humid state. The content of combined lobeline hydrochloride is 6.3% by mass. The time of absorption of the pharmaceutical preparation in the mouth cavity is 2.4 hours.

EXAMPLE 14

Monocarboxycellulose taken in the amount of 2 g and prepared as in Example 8 hereinbefore is placed in 100 ml of an aqueo-ethanolic (1:25 by volume) solution containing 1.7 g of lobeline hydrochloride, kept in this solution for 5 hours at room temperature under continuous stirring. The resulting sample is dried at room temperature to the air-humid state. The content of combined lobeline hydrochloride is 13.9% by mass. The time of absorption of the pharmaceutical preparation in the mouth cavity is 2.3 hours.

EXAMPLE 15

Hydroxystarch taken in the amount of 2 g is placed into 100 ml of a 1% aqueo-ethanolic solution (1:8 by volume) of cytisine, added with 1.2 ml of a 1N solution of HCl to the pH value of 6.9 and kept for two hours at the temperature of 12° C. The resulting sample is dried at room temperature to the air-humid state. The content of combined cytisine determined by the Kjeldahl method is 40% by mass. The time of absorption of the pharmaceutical preparation in the mouth cavity is 4 hours.

EXAMPLE 16

Dicarboxydextran taken in the amount of 2 g is placed into 100 ml of a 1% aqueo-ethanolic (1:2 by volume) solution of lobeline hydrochloride, added with 4.2 ml of a 0.1N solution of NaOH to the pH value of 6.5, kept for 4 hours at the temperature of 15° C. The resulting sample is dried at room temperature to the air-humid state. The content of combined lobeline hydrochloride determined by the Kjeldahl method is equal to 5% by mass. The time of absorption of the pharmaceutical preparation in the mouth cavity is 8 hours.

EXAMPLE 17

Polymethacrylic acid taken in the amount of 2 g is placed into 100 ml of a 1% aqueo-ethanolic (1:25 by volume) solution of cytisine at the pH=8.5, kept for 3 hours at the temperature of 8° C. The resulting sample is dried at room temperature to the air-humid state. The content of combined cytisine determined by the Kjeldahl method is 20% by mass. The time of absorption of the preparation in the mouth cavity is 10 hours.

EXAMPLE 18

Polyvinylsulphate taken in the amount of 2 g is placed into 100 ml of a 1% aqueo-ethanolic solution (1:6 by volume) of anabasine hydrochloride, added with 4.5 ml of a 0.1N solution of NaOH to the pH value of 7, maintained for 2 hours at the temperature of 8° C. The resulting sample is dried at room temperature to the air-humid state. The content of combined anabasine determined by the Kjeldahl method is 2.7% by mass. The time of absorption of the preparation in the mouth cavity is 2 hours.

EXAMPLE 19

Sulphodextran taken in the amount of 2 g is placed in 100 ml of a 1% aqueo-isopropanolic (1:8 by volume) solution of anabasine hydrochloride, added with 4.2 ml of a 0.1N solution of NaOH to the pH value of 6.5, kept for 3 hours at the temperature of 8° C. The resulting sample is dried at room temperature to the air-humid state. The content of combined anabasine determined by the Kjeldahl method is 3.2% by mass. The time of absorption of the preparation in the mouth cavity is 4 hours.

EXAMPLE 20

Carboxymethylcellulose taken in the amount of 2 g is placed in 100 ml of a 1% aqueo-ethanolic (1:6 by volume) solution of lobeline hydrochloride, added with 3.8 ml of a 1N solution of NaOH to the pH=6.5, kept for 3 hours at the temperature of 8° C. The resulting sample is dried at room temperature to the air-humid state. The content of combined lobeline hydrochloride determined by the Kjeldahl method is 8.2% by mass. The time of absorption of the preparation in the mouth cavity is 6 hours.

EXAMPLE 21

Cellulose taken in the amount of 2 g is placed into a solution containing 3.52 ml of $H_3PO_4$ (density 1.72 $g/cm^3$), 14.8 g of urea and 2.4 ml of water, maintained for 30 minutes at the temperature of 80° C., extracted from the solution, squeezed to the mass of 4.2 g, dried at the temperature of 50° C. for 24 hours. The resulting sample is heat-treated for one hour at the temperature of 145° C., washed for 4 times with hot water (water temperature is 90° C.), 2 times with water at room temperature, then poured with 100 ml of a 0.1N solution of HCl, kept for 2 hours at room temperature. Thereafter, the removed sample is rinsed with water till the disappearance of the qualitative reaction for the $Cl^-$ ion, dried at room temperature till the air-humid state. The content of phosphoric-acid groups is 2.97 mg-equiv/g.

Phosphatecellulose taken in the amount of 2 g is placed in 55 ml of a 1% aqueo-ethanolic (10:1 by volume) solution of cytisine, added with 1 ml of a 1N solution of hydrochloric acid to the pH value of 7.5, kept for 3 hours at the temperature of 15° C. The resulting sample is dried at room temperature till the air-humid state. The content of combined cytisine determined by the Kjeldahl method is 39.8% by mass. The time of absorption of the pharmaceutical preparation in the mouth cavity is 13 hours.

EXAMPLE 22

Phosphate cellulose prepared in a manner similar to that described in the foregoing Example 21 and taken in the amount of 2 g is placed in 100 ml of a 1% aqueo-ethanolic (1:3 by volume) solution of lobeline hydrochloride, added with 4.5 ml of a 0.1N solution of NaOH to the pH value of 7.2, kept for 4 hours at the temperature of 15° C. The thus-obtained sample is dried at room temperature to the air-humid state. The content of combined lobeline hydrochloride is 20% by mass. The time of absorption of the pharmaceutical preparation in the mouth cavity is 15 hours.

EXAMPLE 23

Into a heated vessel there are charged 20 kg of a modified larch balsam and heated to the temperature of 75° C. till a complete melting of the mass under stirring. Under continuous stirring the molten base is gradually added with 1.5 kg of a plastifying agent (sunflower oil), 12 kg of syrup, 0.6 kg of an aromatizing agent (orange oil) and 61.9 kg of sugar powder.

The final chewing mass with the temperature of 51° C. is discharged from the heated vessel and delivered to forming. During the forming the chewing gum composition is incorporated with monocarboxycellulose in the form of a knitted web modified with anabasine hydrochloride according to the procedure described in Example 6 hereinbefore, the components being present in the following proportions, per cent by mass:

| | |
|---|---|
| anabasine hydrochloride | 2.5 |

| | |
|---|---|
| monocarboxycellulose | 97.5 |

As a result, every formed piece of the chewing gum with the mass of 3 g contains 0.12 g of modified (with anabasine hydrochloride) polymer which is 4% by mass of the total mass of the chewing gum.

EXAMPLE 24

Into a heated vessel there are charged 31 kg of a synthetic base available from a French company "Dreifus" and heated to a complete melting of the mass at the temperature of 75° C. under stirring. The molten base is gradually added, under continuous stirring, with 1 kg of a plastifying agent (glycerol), 19 kg of syrup, 0.4 kg of an aromatizing agent (peppermint oil) and 48.4 kg of sugar powder.

The final chewing mass with the temperature of 51° C. is discharged from the heated vessel and delivered to forming. During the forming the chewing gum composition is incorporated with phosphatecellulose in the form of a fibre modified, according to the procedure described in Example 22, with lobeline hydrochloride at the following proportions of the components, per cent by mass:

| | |
|---|---|
| lobeline hydrochloride | 20.0 |
| phosphatecellulose | 80.0 |

As a result, every formed piece of the chewing gum with the mass of 5 g contains 0.01 g of a polymer modified with lobeline hydrochloride which constitutes 0.2% by mass of the total mass of the chewing gum composition.

EXAMPLE 25

Into a heated vessel there are charged 12.5 kg of a modified larch balsam and 12.5 kg of a synthetic base available from "Dreifus", a French company, and heated at the temperature of 75° C. till a complete melting of the mass under stirring. The molten base is gradually added, under continuous stirring, with 1.2 kg of a plasticizer (glycerol), 15.5 kg of syrup, 0.5 kg of an aromatizing agent (peppermint oil) and 57.8 kg of sugar powder.

The ready chewing mass with the temperature of 50° C. is disharged from the heated vessel and delivered to forming. During the forming, into the chewing gum composition monocarboxycellulose is incorporated in the form of a thread-like fibre modified according to the procedure described in Example 3 hereinbefore with cytisine at the following proportions of the components, per cent by mass:

| | |
|---|---|
| cytisine | 40 |
| monocarboxycellulose | 60 |

As a result, every formed piece of the chewing gum with the mass of 5 g contains 0.0025 g of a cytisine-modified polymer which is 0.05% by mass of the total mass of the chewing gum.

EXAMPLE 26

A chewing mass produced in a manner similar to that described in Example 25, is discharged from a heated vessel at the temperature of 51° C. During the forming into the chewing gum composition phosphatecellulose modified with pyrroxane is additionally introduced in the amount of 10% by the total mass of the chewing gum.

EXAMPLE 27

A chewing mass produced in a manner similar to that described in Example 24 hereinbefore is discharged from a heated vessel and cooled to the temperature of 43° C. During the forming into the chewing composition additionally introduced is aminocarboxycellulose modified with ascorbic acid and taken in the amoount of 5% of the total mass of the chewing gum.

INDUSTRIAL APPLICABILITY

The pharmaceutical antinicotine-effect preparation according to the present invention is intended to facilitate giving-up smoking and for the treatment of nicotinism.

I claim:

1. A pharmaceutical preparation in the form of a chewing gum effective to facilitate giving-up smoking and for the treatment of nicotinism comprising, an alkaloid in an amount of 2.5 to 40.0 percent by weight of the preparation selected from a member of the group consisting of cystisine, anabasine, lobeline and nontoxic salts thereof and a biologically absorbable polymeric vehicle containing a cation exchange group chemically combined with said alkaloid through said cation exchange group, wherein the polymeric vehicle is selected from a member of the group consisting of monocarboxycellulose, carboxymethylcellulose, phosphatecellulose, polyvinyl sulfate, polymethacrylic acid, discarboxydextran and hydroxystarch, a base, a plastifying agent, syrup, and aromatizing agent, sugar powder at the following proportions of the components, percent by mass: polymeric vehicle modified by:

| | |
|---|---|
| alkaloid | 0.05–4 |
| a base | 20–31 |
| plastifying agent | 1–1.5 |
| syrup | 12–19 |
| aromatizing agent | 0.4–0.6 |
| sugar powder | the balance |

2. A method for producing a pharmaceutical preparation effective to facilitate giving-up smoking and for the treatment of nicotinism, the preparation comprising an alkaloid in an amount of 2.5 to 40.0 percent by weight of the preparation selected from a member of the group consisting of cystisine, anabasine, lobeline and nontoxic salts thereof and a biologically absorbable polymeric vehicle containing a cation exchange group chemically combined with said alkaloid through said cation exchange group, wherein the polymeric vehicle is selected from a member of the group consisting a monocarboxycellulose, carboxymethylcellulose, phosphatecellulose, polyvinylsufate, polymethacrylic acid, dicarboxydextran and hydroxystarch, the method comprising a method in which the biologically absorbable polymeric vehicle containing a cation-exchange group is reacted with said alkaloid effective to block the nicotine receptor zones of the mucous membrane of the mouth in an aqueousorganic medium at a volume ratio between the aqueous and organic phases of 1–15: 1–25 respectively at a temperature within the range of from 8° to 22° C.

3. A method according to claim 2, in which the interaction between said components is effected at a pH of the medium ranging from 6.5 to 8.5.

4. A method according to claim 2, in which aqueous ethanol or an aqueous-isopropanol medium is used.

5. A pharmaceutical preparation effective to facilitate giving-up smoking and for the treatment of nicotinism comprising an active component comprised of an alkaloid in an amount of 2.5 to 40.0% by weight of the active component selected from a member of the group consisting of cystisine, anabasine, lobeline and nontoxic salts thereof and a biologically absorbable polymeric vehicle containing a cation exchange group chemically combined with said alkaloid through said cation exchange group, wherein the polymeric vehicle is selected from a member of the group consisting of monocarboxycellulose, carboxymethylcellulose, phosphatecellulose, polyvinylsulfate, polymethacrylic acid, dicarboxydextran and hydroxystarch in an amount effective for the treatment of nicotinism, in combination with phosphate cellulose modified by pyrroxane in an amount of 5 to 10% of the preparation and a pharmaceutically acceptable vehicle.

6. The pharmaceutical preparation according to claim 5 in which the active component is anabasine hydrochloride chemically combined with carboxymethylcellulose.

7. The pharmaceutical preparation according to claim 6 in which the pharmaceutically acceptable vehicle is chewing gum.

8. A pharmaceutical preparation effective to facilitate giving-up smoking and for the treatment of nicotinism comprising an active component comprised of an alkaloid in an amount of 2.5 to 40% by weight of the active component selected from a member of the group consisting of cystisine, anabasine, lobeline and nontoxic salts thereof and a biologically absorbable polymeric vehicle containing a cation exchange group chemically combined with said alkaloid through said cation exchange group, wherein the polymeric vehicle is selected from a member of the group consisting of monocarboxycellulose, carboxymethylcellulose, phosphatecellulose, polyvinylsulfate, polymethacrylic acid, dicarboxydextran and hydroxystarch in an amount effective for the treatment of nicotinism, in combination with aminocarboxycellulose modified with ascorbic acid in an amount of 5 to 15% of the preparation and a pharmaceutically acceptable vehicle.

9. The pharmaceutical preparation according to claim 8, in which the active component is anabasine hydrochloride chemically combined with carboxymethylcellulose.

10. The pharmaceutical preparation according to claim 9 in which the pharmaceutically acceptable vehicle is chewing gum.

11. A pharmaceutical preparation in the form of chewing gum effective to facilitate giving-up smoking and for the treatment of nicotinism comprising in percent by mass:

| | |
|---|---|
| an active component comprised of anabasine hydrochloride in an amount of 2.5 to 40 wt. % of the active component and a biologically absorbable polymeric vehicle containing a cation exchange group comprised of carboxymethylcellulose chemically combined with the anabasine hydrochloride through the cation exchange group | 0.05–4 |
| phosphate cellulose modified by pyrroxane | 5–10 |
| a base | 20–31 |
| plastifying agent | 1–1.5 |
| syrup | 12–19 |
| aromatizing agent | 0.4–0.6 |
| sugar powder | the balance. |

12. A pharmaceutical preparation in the form of chewing gum effective to facilitate giving-up smoking and for the treatment of nicotinism comprising in percent by mass:

| | |
|---|---|
| an active component comprised of anabasine hydrochloride in an amount of 2.5 to 40 wt. % of the active component and a biologically absorbable polymeric vehicle containing a cation exchange group comprised of carboxymethylcellulose chemically combined with the anabasine hydrochloride through the cation exchange group amino-carboxycellulose modified by ascorbic acid | 0.05–4 |
| | 5–15 |
| a base | 20–31 |
| plastifying agent | 1–1.5 |
| syrup | 12–19 |
| aromatizing agent | 0.4–0.6 |
| sugar powder | the balance |

* * * * *